(12) United States Patent
Hornung et al.

(10) Patent No.: US 11,474,056 B2
(45) Date of Patent: Oct. 18, 2022

(54) SENSOR FOR DETERMINING THE THERMAL CAPACITY OF NATURAL GAS

(71) Applicant: SENSIRION AG, Stäfa (CH)

(72) Inventors: Mark Hornung, Stäfa (CH); Andreas Rüegg, Stäfa (CH); David Kiliani, Stäfa (CH); Nicolas Möller, Stäfa (CH)

(73) Assignee: SENSIRION AG, Stäfa (CH)

( * ) Notice: Subject to any disclaimer, the term of this patent is extended or adjusted under 35 U.S.C. 154(b) by 0 days.

(21) Appl. No.: 17/051,308

(22) PCT Filed: Apr. 23, 2019

(86) PCT No.: PCT/EP2019/060284
§ 371 (c)(1),
(2) Date: Oct. 28, 2020

(87) PCT Pub. No.: WO2019/211115
PCT Pub. Date: Nov. 7, 2019

(65) Prior Publication Data
US 2021/0048401 A1 Feb. 18, 2021

(30) Foreign Application Priority Data
Apr. 30, 2018 (EP) .................................. 18170159

(51) Int. Cl.
*G01N 25/18* (2006.01)
*G01N 25/00* (2006.01)
*G01N 33/22* (2006.01)

(52) U.S. Cl.
CPC ........... *G01N 25/18* (2013.01); *G01N 25/005* (2013.01); *G01N 33/225* (2013.01)

(58) Field of Classification Search
CPC ..... G01N 25/18; G01N 25/005; G01N 33/225
(Continued)

(56) References Cited

U.S. PATENT DOCUMENTS 7,188,519 B2 3/2007 Hornung et al.
2014/0208830 A1 7/2014 Buhler et al.
(Continued)

FOREIGN PATENT DOCUMENTS

EP 0348245 A2 * 12/1989 ............. G01N 25/18
EP 0439950 A1 8/1991
(Continued)

OTHER PUBLICATIONS

International Search Report and Written Opinon for corresponding International Application No. PCT/EP2019/060284 dated Jun. 26, 2019.

*Primary Examiner* — Mirellys Jagan
(74) *Attorney, Agent, or Firm* — Renner, Otto, Boisselle & Sklar, LLP (57) ABSTRACT

The disclosure concerns a sensor device for determining the thermal capacity of a natural gas. The sensor device comprises a substrate, a recess or opening arranged in the substrate, a first heating component and a first sensing component. The first heating component comprises a first heating structure and a temperature sensor and the first sensing component comprises a temperature sensor. The sensor device is configured to measure the thermal conductivity of the natural gas at a first measuring temperature and at a second measuring temperature. The sensor device is configured to determine a first, in particular a constant, and a second, in particular a linear temperature coefficient of a temperature dependency function of the thermal conductivity and to determine the thermal capacity of the natural gas based on a fitting function. The fitting function is dependent on the first and the second temperature coefficient.

16 Claims, 6 Drawing Sheets

(58) Field of Classification Search
USPC .............. 374/1, 143, 44, 208, 141, 166, 183
See application file for complete search history.

(56) References Cited

U.S. PATENT DOCUMENTS

2017/0016840 A1  1/2017  Bourlon et al.
2019/0079034 A1  3/2019  Falkowski

FOREIGN PATENT DOCUMENTS

| EP | 1947450 A1 | | 7/2008 | |
|----|-----------|---|--------|---|
| EP | 1426740 B1 | | 11/2014 | |
| JP | 2010236890 A | * | 10/2010 | |
| WO | WO-9308457 A1 | * | 4/1993 | ........... G01N 33/225 |
| WO | 2001018500 A1 | | 3/2001 | |
| WO | WO-2016180760 A1 | * | 11/2016 | ............. G01F 1/696 |
| WO | 2017140451 A1 | | 8/2017 | |

* cited by examiner

SENSOR FOR DETERMINING THE THERMAL CAPACITY OF NATURAL GAS

This application is a national phase of International Application No. PCT/EP2019/060284 filed Apr. 23, 2019 and published in the English language, which claims priority to European Application No. EP 18170159.0 filed Apr. 30, 2018, both of which are hereby incorporated herein by reference.

TECHNICAL FIELD

The invention relates to sensor devices for determining the thermal capacity of natural gases.

Further aspects of the invention relate to a sensor system comprising a gas flow sensor and a sensor device for determining the thermal capacity of a natural gas. Further aspects relate to a corresponding method for operating a sensor device and a corresponding computer program product.

BACKGROUND ART

US 2014/0208830 describes a gas sensor having a membrane spanning an opening in a silicon substrate. The membrane forms a hotplate and has an integrated tungsten heater. In addition, a platinum layer, separated from the tungsten heater by a dielectric layer, forms electrodes for measuring the resistance of a patch of sensing material.

Measurements of the thermal conductivity of fluids with thermal membrane sensors are e.g. described in WO 0118500 A1 or in EP 1426740 B1.

DISCLOSURE OF THE INVENTION

It is an object of the present invention to provide a sensor for measuring thermal properties of a natural gas.

According to an embodiment of a first aspect of the invention, there is provided a sensor device for determining the thermal capacity of a natural gas. The sensor device comprises a substrate, a recess or opening arranged in the substrate, a first heating component and a first sensing component, both extending over said recess or opening, and control circuitry. The first heating component comprises a first heating structure and a temperature sensor and the first sensing component comprises a temperature sensor. The sensor device is configured to heat, at a first measuring step, the first heating structure to a first heating temperature and to measure, at the first measuring step, by the temperature sensor of the first sensing component, temperature changes at the first sensing component in dependence on the heating of the first heating structure, thereby measuring the thermal conductivity of the natural gas at a first measuring temperature. The sensor device is further configured to heat, at a second measuring step, the first heating structure to a second heating temperature and to measure, at the second measuring step, by the temperature sensor of the first sensing component, temperature changes at the first sensing component in dependence on the heating of the first heating structure, thereby measuring the thermal conductivity of the natural gas at a second measuring temperature. The second heating temperature is different from the first heating temperature. The sensor device is configured to determine a first temperature coefficient, in particular a constant temperature coefficient, in particular a non-zero constant temperature coefficient of a temperature dependency function of the thermal conductivity. The sensor device is configured to determine a second, in particular a linear temperature coefficient of the temperature dependency function of the thermal conductivity. The sensor device is further configured to determine the thermal capacity of the natural gas based on a fitting function. The fitting function is dependent on the first and the second temperature coefficient.

Such a sensor device provides an improved accuracy of the thermal capacity measurement. Embodiments of the invention are based on a discovery of the inventors that by measuring not only the thermal conductivity, but also parameters of the temperature dependency of the thermal conductivity, namely at least a first and a second temperature coefficient of the temperature dependency function, may significantly improve the measurement accuracy of the thermal capacity. More particularly, the sensor device uses a fitting function that takes at least the first and the second temperature coefficient as input and provides as output the corresponding thermal capacity of the natural gas. In other words, the fitting function provides a mapping between the measured first and second temperature coefficient and the thermal capacity.

The fitting function may be derived e.g. by numerical methods from a database that comprises a plurality of input data pairs of the first and the second temperature coefficient of the thermal conductivity and the corresponding thermal capacity of the natural gas. As an example, a least means square method may be used. The fitting function may be determined for various compositions of the natural gas. The fitting function may also be denoted as correlation function.

The substrate may be e.g. a silicon substrate, and it forms a mechanical frame of the sensor. It can optionally comprise circuitry integrated thereon, in particular CMOS circuitry, and more particularly CMOS circuitry adapted to control the heating structures and to read out the sensor.

Such an embodied sensor device has at least one heating component and at least one sensing component, wherein the at least one heating component heats its surrounding, in particular the interspace between the first heating component and the first sensing component. This increases the temperature of the fluid/gas in the interspace and in particular at the sensing component. The device performs subsequently at least two measurements with two different heating temperatures and senses the corresponding temperature change at the first sensing component. The respective temperature change is a measure of the thermal conductivity of the natural gas in the interspace at the respective temperature of the interspace. It should be noted that the temperature of the natural gas in the interspace is usually not constant, but there will be a temperature gradient between the heating component and the sensing component. Hence the thermal conductivity which is measured in the first and the second measuring step, is preferably allocated to an intermediate temperature between the respective heating temperature and the corresponding sensing temperature at the sensing component. According to embodiments the average temperature between the heating temperature and the corresponding sensing temperature may be regarded as the (average) temperature of the natural gas during the respective measurement.

From these at least two measured thermal conductivities at two different measuring temperatures, the first and the second temperature coefficient of the temperature dependency function of the thermal conductivity may be determined.

A natural gas may be in particular a naturally occurring hydrocarbon gas mixture comprising primarily methane, in particular more than 80% methane. In addition, a natural gas may include other components of varying amounts. Such other components may comprise other higher alkanes, carbon dioxide or nitrogen.

According to an embodiment, the sensor device is configured to heat, at a third measuring step, the first heating structure to a third heating temperature and to measure, at the third measuring step, by the temperature sensor of the first sensing component, temperature changes at the first sensing component in dependence on the heating of the first heating structure, thereby measuring the thermal conductivity of the natural gas at a third measuring temperature. The sensor device is configured to determine from the first, the second and the third measuring step the first temperature coefficient, the second temperature coefficient and a third, in particular a quadratic, temperature coefficient of the temperature dependency function of the thermal conductivity. According to this embodiment the fitting function is dependent on the first, the second and the third temperature coefficient.

This further improves the accuracy of the thermal capacity measurement.

According to an embodiment, the sensor device is configured to compensate, by temperature measurements of the temperature sensor of the first heating component, a drift of the first heating structure.

By measuring the temperature at the first heating structure, a drift of the first heating structure may be compensated. This improves the accuracy of the measurement. In addition, material parameter drifts of the supporting structures of the components may be suppressed and/or compensated.

According to an embodiment, the first heating component and the first sensing component are arranged on a membrane covering the recess or opening, in particular a thin film membrane. According to an embodiment, the membrane is a closed membrane. According to other embodiments, the membrane may comprise one or more through-openings extending from one side of the membrane to the other side of the membrane, e.g. in order to establish a fluid communication between the two membrane sides.

According to an embodiment, the first heating component is a first heating bridge being anchored in the substrate and the first sensing component is a first sensing bridge being anchored in the substrate.

By spanning the recess or opening by means of such bridges, the thermal conductance between the bridges and the substrate can be reduced compared with a thin film membrane. Further, the thermal mass can be reduced. This allows to vary the temperature of the first heating bridge quickly.

The temperature sensors are adapted to measure the temperature of the bridges and for controlling the temperature of the bridges.

According to an embodiment, the sensor device is further configured to heat, at a third measuring step, the first heating structure to a third heating temperature and to measure, at the third measuring step, by the temperature sensor of the first sensing bridge, temperature changes at the first sensing bridge in dependence on the heating of the first heating structure to the third heating temperature. The first, the second and the third heating temperature are different from each other. The embodied sensor device is further configured to determine from the first, the second and the third measuring step the first temperature coefficient, the second temperature coefficient and the third temperature coefficient of the temperature dependency function of the thermal conductivity.

This further improves the accuracy of the measurement.

According to an embodiment, the sensor device comprises a second heating bridge comprising a second heating structure and a temperature sensor. The first sensing bridge is arranged between the first heating bridge and the second heating bridge.

With such an embodied sensor device, the temperature of the relevant gas volume measured can be heated to a higher absolute temperature. Therefore the temperature span of the e.g. 3 different heater temperatures can be expanded. This results in a larger measurement signal span. Furthermore, such a second heating structure improves the homogenity of the temperature distribution between the heating bridges and the sensing bridges. More particularly, the gas surrounding the first sensing bride is heated from both sides. This may reduce the temperature difference between the gas that is close to the heating bridges and the gas that is close to the sensing bridge.

According to an embodiment, the first sensing bridge is arranged centrally between the first heating bridge and the second heating bridge.

This results in a symmetric heating of the gas and a symmetric temperature profile of the temperature of the natural gas.

According to an embodiment, the sensor device comprises a second sensing bridge comprising a temperature sensor, wherein the second sensing bridge is arranged at a different distance to the first heating bridge than the first sensing bridge.

Such an embodiment allows to perform differential measurements. With such differential measurements, the influence of the thermal transition between the heating bridge(s) and the surrounding gas as well as the influence of the thermal transitions between the surrounding gas and the sensing bridge(s) may be eliminated. In other words, the difference between the temperature signals measured at the first sensing bridge and the second sensing bridge depends only on the thermal properties of the surrounding gas.

According to an embodiment, the sensor device comprises a third heating bridge comprising a third heating structure and a temperature sensor. Furthermore, the sensor device comprises a second sensing bridge with a temperature sensor. The second sensing bridge is arranged between the second heating bridge and the third heating bridge. Preferably the first sensing bridge is arranged centrally between the first heating bridge and the second heating bridge and the second sensing bridge is arranged centrally between the second heating bridge and the third heating bridge.

Such an embodiment allows for further advantageous measurements of the thermal conductivity. More particularly, it allows differential measurements with a higher electrical amplification gain.

In particular, such an embodied sensor device may be configured to heat, at a first measuring step, the first, the second and the third heating structure to a first heating temperature and to measure, at the first measuring step, by the temperature sensors of the first and the second sensing bridge, temperature changes at the first sensing bridge and the second sensing bridge in dependence on the heating of the first, the second and the third heating structure. Furthermore, such an embodied sensor device may be configured to heat, at a second measuring step, the first heating structure to a second heating temperature or the first and the second heating structure to the second heating temperature, while the second and the third or only the third heating structure is continued to be heated to the first heating temperature. The second heating temperature is different from the first heating temperature. Then, at the second measuring step, the device measures by the temperature sensors of the first and the second sensing bridge, a differential temperature signal of the temperature difference between the first and the second sensing bridge. Finally, the sensor device may determine from the first and the second measuring step the first temperature coefficient and the second temperature coefficient of the temperature dependency function of the thermal conductivity.

According to an embodiment, the sensor device is configured to heat, at a third measuring step, the first heating structure or the first and the second heating structure to a third heating temperature, while the second and the third or only the third heating structure is continued to be heated to the first heating temperature. The third heating temperature is different from the first and the second heating temperature. Then the device measures, at the third measuring step, by the temperature sensors of the first and the second sensing bridge, a differential temperature signal of the temperature difference between the first and the second sensing bridge and determines from the first, the second and the third measuring step the first, the second and the third temperature coefficient of the temperature dependency function.

According to embodiments, the sensor device may be configured to repeat the first and the second measurement step or the first, the second and the third measurement step with different heating temperatures. This may include to start with a different base temperature.

Such embodiments further increase the sensitivity of the thermal conductivity measurements and the corresponding temperature coefficients.

According to embodiments, the sensor device comprises a housing and the housing comprises a venting medium configured to allow a diffusive fluid exchange between the surrounding of the sensor device and the recess or opening. According to embodiments, the housing forms a "closed" fluid cavity to avoid fluid flow across the sensing and heating bridges. According to embodiments, a "closed fluid cavity" shall mean that a cavity that avoids or suppresses external fluid flows across the heating and sensing bridges, while a diffusive fluid exchange with the surrounding is possible via the venting medium.

According to an embodiment, the venting medium is a film based on or made from one or more of polymer— especially fluoropolymer, PTFE, acrylic copolymer, polyethersulfone polymer—glass fiber, porous organic material or porous inorganic material, e.g. as disclosed in EP2871152.

According to embodiments, the temperature sensors of the first and/or the second sensing bridge are embodied as thermopile elements or resistive elements. According to embodiments, the temperature sensors of the first, the second and/or the third heating bridge are embodied as resistive elements or thermopile elements. According to embodiments, the temperature sensors of the first, the second and/or the third heating bridge and of the first and/or the second sensing bridge are of the same type.

Using the same temperature sensors eliminates the temperature dependence of the temperature sensors in the signal ratio. Additionally, ageing effects on the sensor device are compensated, as all temperature sensors are exposed to the same environmental ageing conditions.

According to embodiments, the sensor device is configured to perform a calibration procedure. The calibration procedure comprises steps of adapting the fitting function to the respective temperature characteristics of the first, the second and/or the third heating bridge and adapting the fitting function to the respective temperature characteristics of the first and/or the second sensing bridge. This improves the accuracy of the thermal capacity measurements.

According to another aspect of the invention, a sensor system is provided which encompasses a gas flow sensor for measuring the gas flow of a target gas and a sensor device according to the first aspect of the invention. The sensor device is configured to determine the thermal capacity of the target gas and to provide the determined thermal capacity of the target gas to the gas flow sensor. The sensor system is configured to compensate the gas dependency of the gas flow sensor by means of the thermal capacity provided by the sensor device.

According to another aspect of the invention, a computer program product for operating a sensor device according to the first aspect is provided. The computer program product comprises a computer readable storage medium having program instructions embodied therewith. The program instructions are executable by the sensor device to cause the sensor device to measure the thermal conductivity of a natural gas at a first temperature, to measure the thermal conductivity of the natural gas at a second temperature, to determine a first and a second temperature coefficient of a temperature dependency function of the thermal conductivity and to determine the thermal capacity of the natural gas based on a fitting function. The fitting function is dependent on the first and the second temperature coefficient.

According to another aspect of the invention, a method for determining the thermal capacity of a natural gas is provided. The method comprises steps of measuring the thermal conductivity of the natural gas at a first temperature and measuring the thermal conductivity of the natural gas at a second temperature. The method comprises further steps of determining a first, in particular a constant, and a second, in particular a linear, temperature coefficient of a temperature dependency function of the thermal conductivity. A further step comprises determining the thermal capacity of the natural gas based on a fitting function which is dependent on the first and the second temperature coefficient.

According to an embodiment of the method, a further step of measuring a third, in particular a quadratic temperature coefficient of the temperature dependency function of the thermal conductivity is provided. According to this embodiment the fitting function is dependent on the first, the second and the third temperature coefficient.

Other advantageous embodiments are listed in the dependent claims as well as in the description below.

BRIEF DESCRIPTION OF THE DRAWINGS

The invention will be better understood and objects other than those set forth above will become apparent from the following detailed description thereof. Such description refers to the annexed drawings, wherein:

FIG. 1b shows a corresponding cross sectional view along line I-I of FIG. 1a;

FIG. 3b shows a corresponding cross sectional view along line III-III of FIG. 3a;

All top views of the bridges of the sensor device may show the dielectric base material and/or the dielectric layers of the bridges in a partly transparent manner to illustrate the embedded heating structures and temperature sensors. The drawings are simplified illustrations to illustrate embodiments of the invention and are not to scale.

MODES FOR CARRYING OUT THE INVENTION

Definitions

Terms such as "top", "bottom", "above", "below" are used in the sense that the side of the substrate that carries the bridges is the top side of the substrate.

Figure 1A:
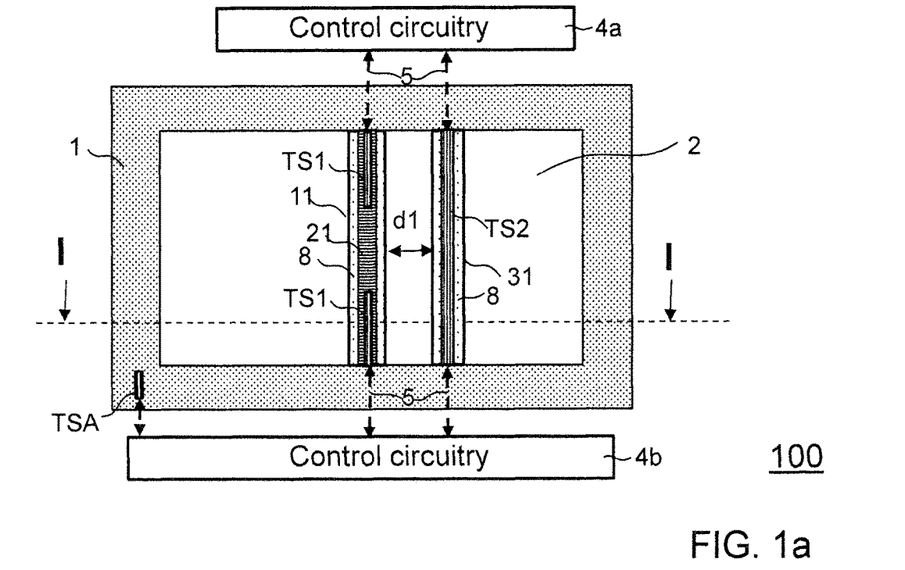
FIG. 1a shows a top view of a sensor for determining the thermal capacity of a natural gas according to an embodiment of the invention.
Figure 1B:
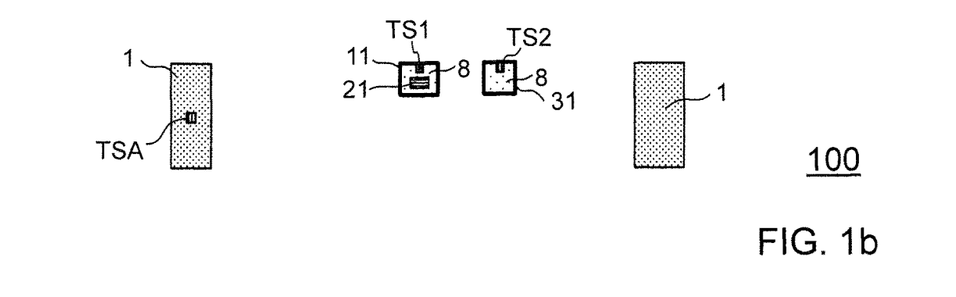

FIG. 1a shows a top view of a sensor device 100 for determining the thermal capacity of a natural gas. FIG. 1b shows a corresponding cross sectional view along line I-I of FIG. 1a.

The sensor device is in particular suited for determining the thermal capacity of natural gases. Such a natural gas may be in particular a naturally occurring hydrocarbon gas mixture comprising primarily methane, but often also including other components of varying amounts. Such other components may comprise other higher alkanes, carbon dioxide or nitrogen. According to embodiments, the natural gases comprise more than 80% methane.

The sensor device 100 comprises a substrate 1, in particular a substrate of silicon. The substrate 1 has an opening or recess 2 arranged therein. The sensor 100 comprises a plurality of separate bridges that span this opening or recess 2.

More particularly, the sensor 100 comprises as first heating component a first heating bridge 11 and as first sensing component a first sensing bridge 31, both extending over the recess or opening 2 and being anchored in the substrate 1. The first heating bridge 11 and the first sensing bridge 31 may be formed by a plurality of dielectric layers, metal layers and poly-silicon layers. The metal layers or the poly-silicon layers may form heating structures and temperature sensors as will be described in more detail below. The dielectric layers may in particular comprise layers of silicon oxide and/or silicon nitride as dielectric base material of the respective bridges. The first heating bridge 11 comprises a first heating structure 21, a temperature sensor TS1 and a dielectric base material 8 of e.g. silicon oxide. The first heating structure 21 and the temperature sensor TS1 are electrically insulated from each other by the base material 8. The first sensing bridge 31 comprises a temperature sensor TS2 and a dielectric base material 8. The temperature sensor TS1 is adapted to measure the temperature of the first heating bridge 11 and the temperature sensor TS2 to measure the temperature of the first sensing bridge 31. The sensor device 100 further comprises control circuitry 4a, 4b for controlling the operation of the sensor device 100. The control circuitry 4a, 4b may be embodied as integrated circuitry 4a and 4b into the substrate 1. The control circuitry 4a, 4b includes circuitry for driving the first heating structure 21 and for processing signals from the temperature sensors TS1 and TS2. For this, the control circuitry 4a and 4b is electrically connected to the first heating structure 21 and the temperature sensors TS1, TS2 via interconnect circuitry 5. Advantageously, control circuitry 4a, 4b is integrated in CMOS technology. According to embodiments, the whole sensor device may be compatible with current CMOS manufacturing processes. Having the CMOS circuitry on-board of substrate 1 allows to reduce the number of bonds to the substrate and to increase signal-to-noise ratio.

The sensor device 100 may further comprise an ambient temperature sensor TSA for sensing or measuring the ambient temperature of the sensor device 100. The ambient temperature sensor TSA may be in particular integrated into the substrate 1 and may hence in particular be configured to measure or sense the temperature of the substrate 1. The ambient temperature sensor TSA is arranged in particular outside the range of influence of the heating structures of the sensor device, i.e. in this example outside the range of influence of the first heating structure 11.

Structures of the type shown in FIG. 1 can e.g. be built using techniques such as described in EP 2278308 or US 2014/0208830.

In particular, the process for manufacturing comprises the steps of forming a plurality of dielectric and metal layers on top of substrate 1. Some of these layers may be deposited in the course of the process for forming the CMOS circuitry 4a, 4b, e.g. as inter-metal dielectric layer and metal layers, while other layers may be applied during post-processing, such as a tensile silicon nitride layer. Then, recess or opening 2 is formed using selective, anisotropic etching techniques.

As illustrated in FIG. 1, the first heating bridge 11 is arranged at a distance $d_1$ from the first sensing bridge 31.

The temperature sensors TS1 and TS2 may be thermopile elements or resistive elements. Preferably the temperature sensors TS1 and TS2 are of the same type. The resistive elements may be formed e.g. by poly-silicon. The thermopile elements may be formed e.g. by a pair of metal and poly-silicon. The temperature sensor TSA is embodied as a temperature sensor that can measure the absolute temperature and may be e.g. embodied as a resistive element.

Using the same temperature sensors eliminates the temperature dependence of the temperature sensors. Additionally, ageing effects on the sensor device are compensated, as all temperature sensors are exposed to the same environmental ageing conditions.

In order to measure the thermal capacity of the fluid, in particular the gas that surrounds the first heating bridge 11 and the first sensing bridge 31, in particular the fluid/gas between the first heating bridge 11 and the first sensing bridge 31, the sensor device 100 operates as follows.

Generally, the first heating structure 21 of the first heating bridge 11 is heated to a plurality of different heating temperatures $TH_{1x}$ and the first sensing bridge 31 senses by its temperature sensor TS2 the corresponding temperatures $TS_{1x}$ resulting from the respective heating. The temperature changes depend on the thermal conductivity $\lambda$ of the fluid/gas and hence the ratio $TH_{1x}/TS_{1x}$ is a measure of the thermal conductivity $\lambda$ of the surrounding fluid or gas.

For even more accurate calculations, the ambient temperature, in particular the substrate temperature measured by the ambient temperature sensor TSA, can be taken into account. Such an embodiment takes into account that the measured variable, in particular the ratio $TH_{1x}/TS_{1x}$, may also depend on the ambient temperature of the sensor device. This may be in particular advantageous for sensor devices which are operated in environments with significant temperature changes. According to such an embodiment, the ambient temperature can be determined by the ambient temperature sensor TSA. The sensor device may then take the ambient temperature into account such that the accuracy of the determined thermal conductivity is improved.

More particularly, the ratio $TH_{1x}/TS_{1x}$ is a function $f$ of the thermal conductivity $\lambda$, wherein the function $f$ depends on the ambient temperature TA. This may be expressed as follows:

$$TH_{1x}/TS_{1x} = f_{TA}(\lambda).$$

wherein $f_{TA}(\lambda)$ denotes the function $f$ for the respective ambient temperature TA.

According to embodiments, the sensor device 100 may be calibrated in advance by performing calibration measurements for determining the temperature dependency characteristic of the function $f_{TA}(\lambda)$. More particularly, the sensor device 100 may be calibrated in advance by performing calibration measurements for determining the functions $f_{TA}(\lambda)$ for all or a selected subset of the ambient temperatures TA for the envisaged measurement environment of the sensor device according to the respective sensor specification.

Hence according to embodiments the sensor device may measure the respective ambient temperature TA and may then subsequently use the corresponding function $f_{TA}(\lambda)$ for the measurement of the thermal conductivities and the determination of the first and the second temperature coefficients of the temperature dependency function of the thermal conductivity.

Figure 7:
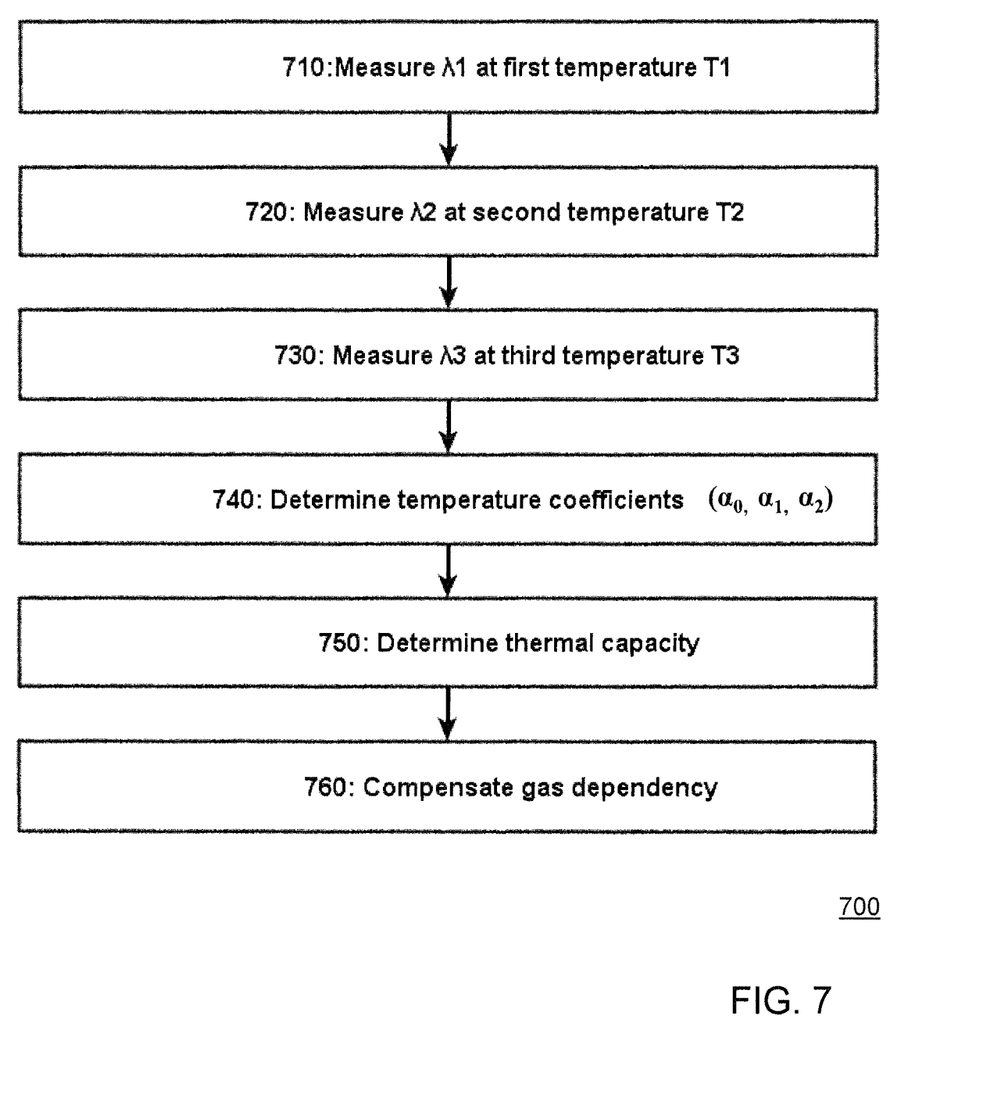
FIG. 7 shows a method for determining the thermal capacity of a natural gas.

In more detail, the sensor device 100 performs, under control of the control circuitry 4a, 4b the measurement steps as illustrated in the flow diagram 700 of FIG. 7. In the following, for ease of illustration, the possible influence of the ambient temperature on the measurement of the thermal conductivity is neglected or not explicitly described.

At a first measuring step 710, the sensor device 100 measures the thermal conductivity $\lambda_1$ of the fluid between the first heating bridge 11 and the first sensing bridge 31 at a first measuring temperature $TM_1$. The first measuring step 710 includes heating the first heating structure 21 of the first heating bridge 11 to a first heating temperature $TH_1$. In response, the temperature sensor TS2 of the first sensing bridge 31 measures a temperature change at the first sensing bridge 31 in dependence on the heating of the first heating structure 21, more particularly a first sensing temperature $TS_{11}$. The ratio $TS_{11}/TH_{11}$ of the first sensing temperature to the first heating temperature is a measure of the thermal conductivity $\lambda_1$ at the first measuring temperature $TM_1$. The first measuring temperature $TM_1$ has a value between the first heating temperature $TH_{11}$ and the first sensing temperature $TS_{11}$. In particular, it may be considered as an average value between the first heating temperature $TH_{11}$ and the first sensing temperature $TS_{11}$, wherein the first sensing temperature $TS_{11}$ is lower than the first heating temperature $TH_{11}$.

Then, at a second measuring step 720, the sensor device 100 measures the thermal conductivity $\lambda_2$ of the fluid at a second measuring temperature $TM_2$. The second measuring step 720 includes heating the first heating structure 21 of the first heating bridge 11 to a second heating temperature $TH_{12}$. In response, the temperature sensor TS2 of the first sensing bridge 31 measures a temperature change at the first sensing bridge 31 in dependence on the heating of the first heating structure 21, more particularly a second sensing temperature $TS_{12}$. The ratio $TS_{12}/TH_{12}$ of the second sensing temperature to the second heating temperature is a measure of the thermal conductivity $\lambda_2$ at the second measuring temperature $TM_2$. The second measuring temperature $TM_2$ has again a value between the second heating temperature $TH_{12}$ and the second sensing temperature $TS_{12}$.

Next, at a third measuring step 730, the sensor device 100 measures the thermal conductivity $\lambda_3$ of the fluid at a third measuring temperature $TM_3$. The third measuring step 730 includes heating the first heating structure 21 of the first heating bridge 11 to a third heating temperature $TH_{13}$. In response, the temperature sensor TS2 of the first sensing bridge 31 measures a temperature change at the first sensing bridge 31 in dependence on the heating of the first heating structure 21, more particularly a third sensing temperature $TS_{13}$. The ratio $TS_{13}/TH_{13}$ of the third sensing temperature to the third heating temperature is a measure of the thermal conductivity $\lambda_3$ at the third measuring temperature $TM_3$. The third measuring temperature $TM_3$ has again a value between the third heating temperature $TH_{13}$ and the third sensing temperature $TS_{13}$.

At a step 740, the control circuitry 4a, 4b determines from the first, the second and the third measuring steps 710-730 a first, a second and a third temperature coefficient of the temperature dependency function of the thermal conductivity $\lambda$. According to embodiments, the temperature dependency function $\lambda(T)$ is a quadratic function:

$$\lambda(T) = \alpha_0 + \alpha_1 T + \alpha_2 T^2; \text{ wherein}$$

$\alpha_0$ is the first constant temperature coefficient, $\alpha_1$ the second linear temperature coefficient and $\alpha_2$ the third quadratic temperature coefficient.

With the three measured thermal conductivities $\lambda_1$, $\lambda_2$ and $\lambda_3$ and the corresponding measuring temperatures TM1, TM2 and TM3, the sensor circuitry has a system with three equations and three unknowns. Accordingly, the control circuitry 4a, 4b can determine the first, the second and the third temperature coefficients $\alpha_0$, $\alpha_1$ and $\alpha_2$ respectively of the temperature dependency function $\lambda(T)$, e.g. by addition and subtraction methods well known to a skilled person in the art.

According to another embodiment, the sensor device may only perform the first and the second measurement steps 710 and 720. It may then determine from the first and the second measuring steps 710 and 720 a first and a second temperature coefficient of the temperature dependency function of the thermal conductivity $\lambda$. According to such an embodiment, the temperature function $\lambda(T)$ is a linear function:

$$\lambda(T) = \alpha_0 + \alpha_1 T; \text{ wherein}$$

$\alpha_0$ is the first constant temperature coefficient and $\alpha_1$ the second linear temperature coefficient.

With the two measured thermal conductivities $\lambda_1$ and $\lambda_2$, the sensor circuitry 4a, 4b has a linear system with two equations and two unknowns. Accordingly, the control circuitry 4a, 4b can determine the first and the second temperature coefficients $\alpha_0$ and $\lambda_1$.

Next, at a step 750, the control circuitry 4a, 4b determines the thermal capacity of the natural gas, in particular the volumetric thermal capacity $c_p\rho$ of the natural gas based on a fitting function $f_{fit}$:

$$c_p\rho = f_{fit}(\alpha_0, \alpha_1, \alpha_2);$$

wherein $c_p$ is the specific heat capacity at constant pressure in J/gK and $\rho$ is the density in g/m³.

Hence according to embodiments the thermal capacity is measured as volumetric thermal capacity $c_p\rho$ in J/(Km³). The volumetric thermal capacity $c_p\rho$ may also be denoted as volumetric heat capacity, also termed volume-specific heat capacity. The volumetric heat capacity describes the ability of a given volume of a fluid to store internal energy while undergoing a given temperature change, but without undergoing a phase transition.

The volumetric heat capacity may be regarded as a 'per unit volume' measure of the relationship between thermal energy and temperature of a fluid.

Embodiments of the invention take advantage of the fact that the thermal conductivity (heat conductivity) of gases is almost pressure independent above 500 mbar, i.e. at atmospheric conditions. Accordingly, embodiments of the invention correlate by means of the fitting function $f_{fit}$ the measured pressure independent thermal conductivity to the standardized heat capacity $cp^*\rho_{ref}$ at standard conditions, i.e. to the heat capacity at reference temperature 0° C. and reference pressure 1013 mbar.

The fitting function $f_{fit}$ is dependent on the first, the second and the third temperature coefficients $\alpha_0$, $\alpha_1$ and $\alpha_2$. The fitting function $f_{fit}$ provides a mapping between the measured first, second and third temperature coefficients and the thermal capacity.

The fitting function $f_{fit}$ may be derived e.g. by numerical methods from a database that comprises a plurality of input data triples of the first, the second and the third temperature coefficient of the thermal conductivity or input data pairs of the first and the second temperature coefficient respectively as well as the corresponding thermal capacity of the natural gas(s). As an example, least squares methods may be used. As another example, robust regression methods may be used. According to embodiments, the fitting function may be determined for various compositions of the natural gas. According to embodiments, the fitting function may be derived from input data triples or input data pairs which represent real data of natural gas compositions that occur on earth.

According to other embodiments, the fitting function may be derived from input data triples or input data pairs which represents real data of essentially all main natural gas compositions that occur in a predefined region of the world. The latter embodiment may be used to enhance the accuracy of the sensor for local or regional applications in a specific region of the world. This may be in particular useful for regions with specific characteristic compositions of the respective natural gases.

Investigations of the applicant have shown that in particular for natural gases the correlation between the measured heat conductivity and the corresponding heat capacity can be significantly approved by methods as described above. As illustrated, embodiments of the invention measure the heat conductivity at least at 2 different temperatures to get the linear temperature coefficient of the heat conductivity, or more preferably at least at 3 different temperatures to get the linear and quadratic temperature coefficients.

The method 700 may comprise a further step 760 at which the determined thermal capacity is used to compensate the gas dependency of a thermal flow sensor. This will be illustrated further below with reference to FIG. 6.

Figure 2:
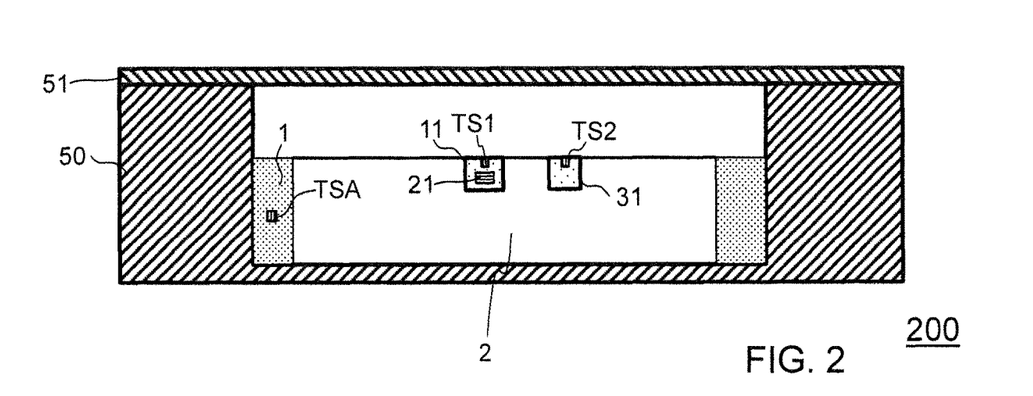
FIG. 2 shows a schematic cross sectional view of a sensor device according to an embodiment of the invention embedded in a housing comprising a venting medium for diffusive fluid exchange.

FIG. 2 shows a schematic cross sectional view of a sensor device 200 according to an embodiment of the invention. The sensor device 200 comprises a housing 50. The housing 50 encompasses a venting medium 51 which allows a diffusive fluid/gas exchange between the surrounding of the sensor device 200 and the recess or opening 2. Such a housing avoids disturbances of the measured signals and improves the measurement accuracy.

Figure 3A:
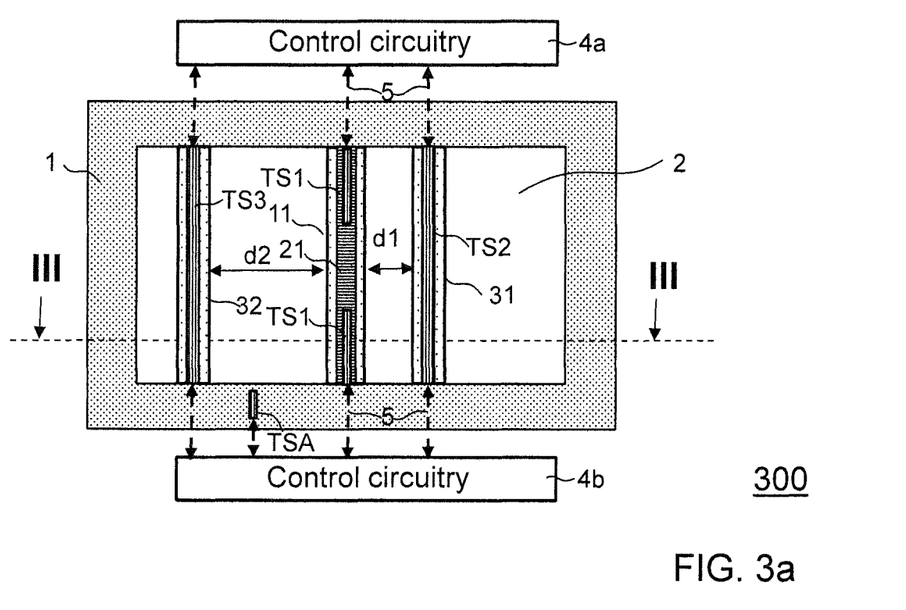
FIG. 3a shows a top view of another sensor device comprising two sensing bridges and one heating bridge.
Figure 3B:
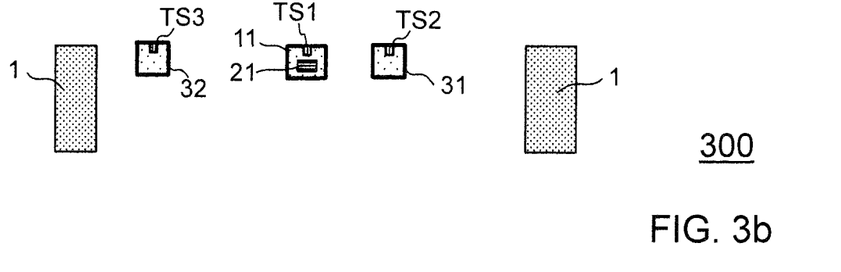

FIG. 3a shows a top view of a sensor device 300 for determining the thermal capacity of a natural gas. FIG. 3b shows a corresponding cross sectional view along line III-III of FIG. 3a. The sensor device 300 corresponds largely to the sensor device 100 of FIG. 1 and hence comprises a substrate 1 having an opening or recess 2, a first heating bridge 11 and a first sensing bridge 31, both extending over the recess or opening 2 and being anchored in the substrate 1. The first heating bridge 11 comprises a first heating structure 21 and a temperature sensor TS1. The first sensing bridge 31 comprises a temperature sensor TS2. The sensor device 300 further also comprises control circuitry 4a, 4b for controlling the operation of the sensor device 100 via interconnect circuitry 5. In addition, the sensor device 300 comprises a second sensing bridge 32 comprising a temperature sensor TS3. The second sensing bridge 32 is arranged at a distance $d_2$ to the first heating bridge 11, while the first sensing bridge 31 is arranged at a different distance $d_1$ to the first heating bridge 11.

The different distances $d_1$ and $d_2$ can be used to perform differential measurements in order to eliminate the thermal transitions between the fluid/gas and the respective bridge. As an example, the ratio $(TS_{1X}-TS_{2X})/TH_{1X}$ could be taken as a measure of the thermal conductivity $\lambda_1$ at the respective measuring temperature $TM_X$, wherein $TS_{1X}$ denotes the measured temperature at the first sensing bridge 31, $TS_{2X}$ the measured temperature at the second sensing bridge 32 and $TH_{1X}$ the heating temperature at the first heating bridge 11 for a measurement X.

The sensor device 300 may further comprise an ambient temperature sensor TSA for sensing or measuring the ambient temperature of the sensor device 300.

Figure 4:
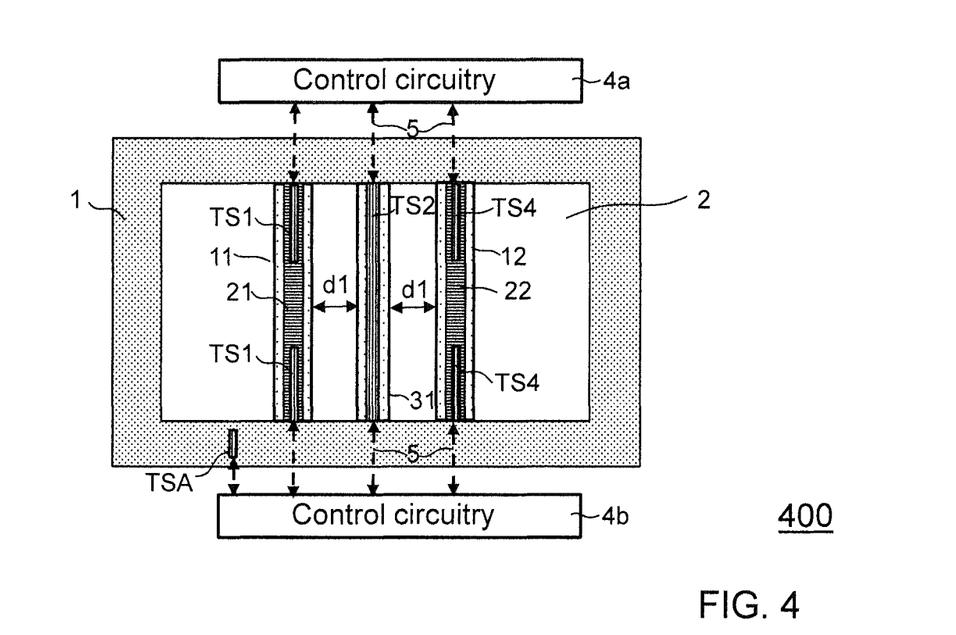
FIG. 4 shows a top view of another sensor device comprising two heating bridges and one sensing bridge.

FIG. 4 shows a top view of a sensor device 400 for determining the thermal capacity of a natural gas. The sensor device 400 corresponds largely to the sensor device 400 of FIG. 1 and hence comprises a substrate 1 having an opening or recess 2, a first heating bridge 11 and a first sensing bridge 31, both extending over the recess or opening 2 and being anchored in the substrate 1. The first heating bridge 11 comprises a first heating structure 21 and a temperature sensor TS1. The first sensing bridge 31 comprises a temperature sensor TS2. The sensor device 400 further also comprises control circuitry 4a, 4b for controlling the operation of the sensor device 100 via interconnect circuitry 5. In addition, the sensor device 400 comprises a second heating bridge 12 comprising a second heating structure 22 and a temperature sensor TS4. The first sensing bridge 31 is arranged centrally between the first heating bridge 11 and the second heating bridge 12. More particularly, both the first heating bridge 11 and the second heating bridge 12 are arranged at a distance $d_1$ to the first sensing bridge 31.

As both the first heating structure 11 and the second heating structure 12 heats the gas which surrounds the first sensing bridge 31, the temperature gradient of the heated gas may be reduced and the temperature profile of the heated gas may be more uniform.

The sensor device 400 may further comprise an ambient temperature sensor TSA for sensing or measuring the ambient temperature of the sensor device 400.

Figure 5:
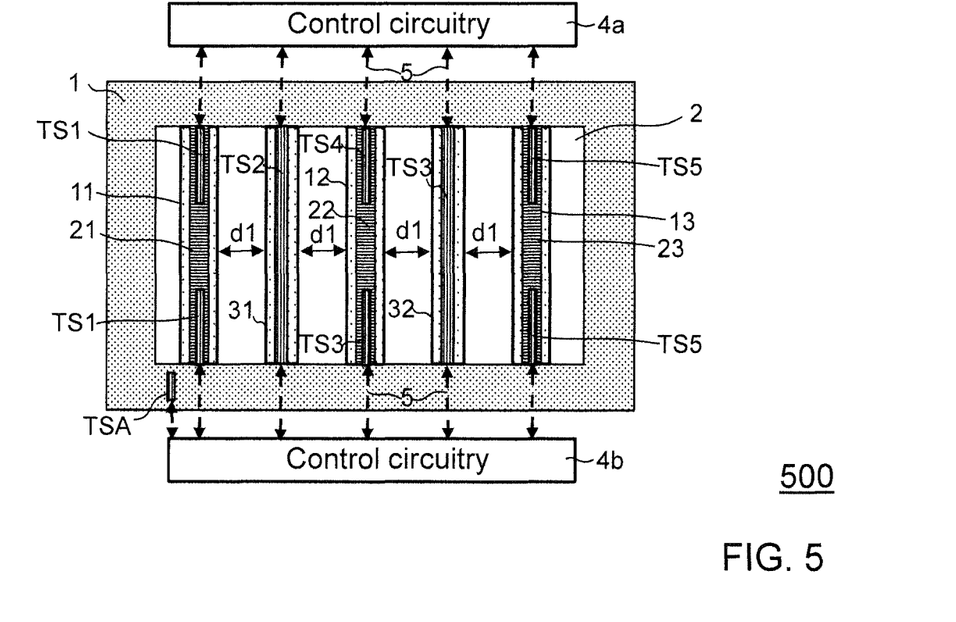
FIG. 5 shows a top view of another sensor device comprising three heating bridges and two sensing bridges.

FIG. 5 shows a top view of a sensor device 500 for determining the thermal capacity of a natural gas. The sensor device 500 corresponds largely to the sensor device 400 of FIG. 4 and hence comprises a substrate 1 having an opening or recess 2, a first heating bridge 11 and a first sensing bridge 31, both extending over the recess or opening 2 and being anchored in the substrate 1. The first heating bridge 11 comprises a first heating structure 21 and a temperature sensor TS1. The first sensing bridge 31 comprises a temperature sensor TS2. Furthermore, the sensor device 500 comprises a second heating bridge 12 comprising a second heating structure 22 and a temperature sensor TS4. The sensor device 500 further also comprises control circuitry 4a, 4b for controlling the operation of the sensor device 100 via interconnect circuitry 5. In addition, the sensor device 500 comprises a third heating bridge 13 comprising a third heating structure 23 and a temperature sensor TS5. Furthermore, the sensor device 500 comprises a second sensing bridge 32 comprising a temperature sensor TS3. The first sensing bridge 31 is arranged centrally between the first heating bridge 11 and the second heating bridge 12 and the second sensing bridge 32 is arranged centrally between the second heating bridge 12 and the third heating bridge 13. More particularly, the first heating bridge 11 and the second heating bridge 12 are arranged at a distance $d_1$ to the first sensing bridge 31 and the second heating bridge 12 and the third heating bridge 13 are arranged at the same distance $d_1$ to the second sensing bridge 32.

The sensor device 500 may further comprise an ambient temperature sensor TSA for sensing or measuring the ambient temperature of the sensor device 500.

The sensor device 500 may operate as follows:

At a first measuring step, the first, the second and the third heating structures 21, 22 and 23 are heated to a first heating temperature $TH_1$.

Then, the sensor device 500 measures, by the temperature sensors TS2 and TS3 of the first sensing bridge 31 and the second sensing bridge 32 respectively temperature changes at the first sensing bridge 31 and the second sensing bridge 32 in dependence on this heating. More particularly, the first sensing bridge 31 measures a temperature signal $TS_{11}$ and the second sensing bridge 32 a temperature signal $TS_{21}$, wherein both signals are substantially the same.

Next, at a second measuring step, the first heating structure 21 is heated to a second heating temperature $TH_2$, which is different, in particular higher than the first heating temperature $TH_1$, while the second heating structure 22 and the third heating structure 23 are continued to be heated to the first heating temperature $TH_1$.

Then, at the second measuring step, the sensor device 500 measures by means of the temperature sensors TS2 and TS3 of the first and the second sensing bridge 31 and 32 respectively a differential temperature signal of the temperature difference between the first sensing bridge 31 and the second sensing bridge 32. More particularly, the first sensing bridge 31 measures a temperature signal $TS_{12}$ and the second sensing bridge 32 a temperature signal $TS_{22}$, wherein $TS_{22}$ is substantially the same as $TS_{11}$ and $TS_{21}$ because the temperature at the second sensing bridge 32 is still mainly influenced by the first heating temperature $TH_1$. Then the sensor device may use the differential temperature signal $TS_{12}-TS_{22}$ or $(TS_{12}-TS_{22})/TS_{11}$. This has the advantage that such a differential measurement can be measured with a higher electrical amplification gain as the starting signal $TS_{11}-TS_{21}$ is close to zero.

From these two measurements, the constant and the linear temperature coefficient may already be determined.

Preferably, a third measuring step is performed. Then, at the third measuring step, the first heating structure 21 is heated to a third heating temperature $TH_3$, which is different, in particular higher than the first heating temperature $TH_1$ and the second heating temperature $TH_2$, while the second heating structure 22 and the third heating structure 23 are continued to be heated to the first heating temperature $TH_1$.

Then, at the third measuring step, the sensor device 500 measures by means of the temperature sensors TS1 and TS2 of the first and the second sensing bridge 31 and 32 respectively another differential temperature signal of the temperature difference between the first sensing bridge 31 and the second sensing bridge 32. More particularly, the first sensing bridge 31 measures a temperature signal $TS_{13}$ and the second sensing bridge 32 a temperature signal $TS_{23}$, wherein $TS_{23}$ is substantially the same as $TS_{11}$, $TS_{21}$ and $TS_{22}$ because the temperature at the second sensing bridge 32 is still mainly influenced by the first heating temperature T1. Then the sensor device may use the differential temperature signal $TS_{13}-TS_{23}$ or $(TS_{13}-TS_{23})/TS_{11}$.

Now the sensor device 500 can determine from the first, the second and the third measuring step the first, the second and the third temperature coefficient of the temperature dependency function.

The sensor device 500 allows very sensitive measurements of the thermal conductivity and the corresponding temperature coefficients.

According to embodiments, the sensor device 500 may be repeat the first and the second measurement step or the first, the second and the third measurement step with a different first heating temperature $TH_1^*$, a different second heating temperature $TH_2^*$ and a different third heating temperature $TH_3^*$. This may further improve the measurement accuracy.

According to other embodiments the temperature of the first and the second heating structure may be increased during the second and the third measuring step, while only the temperature of the third heating structure is kept constant.

Figure 6:
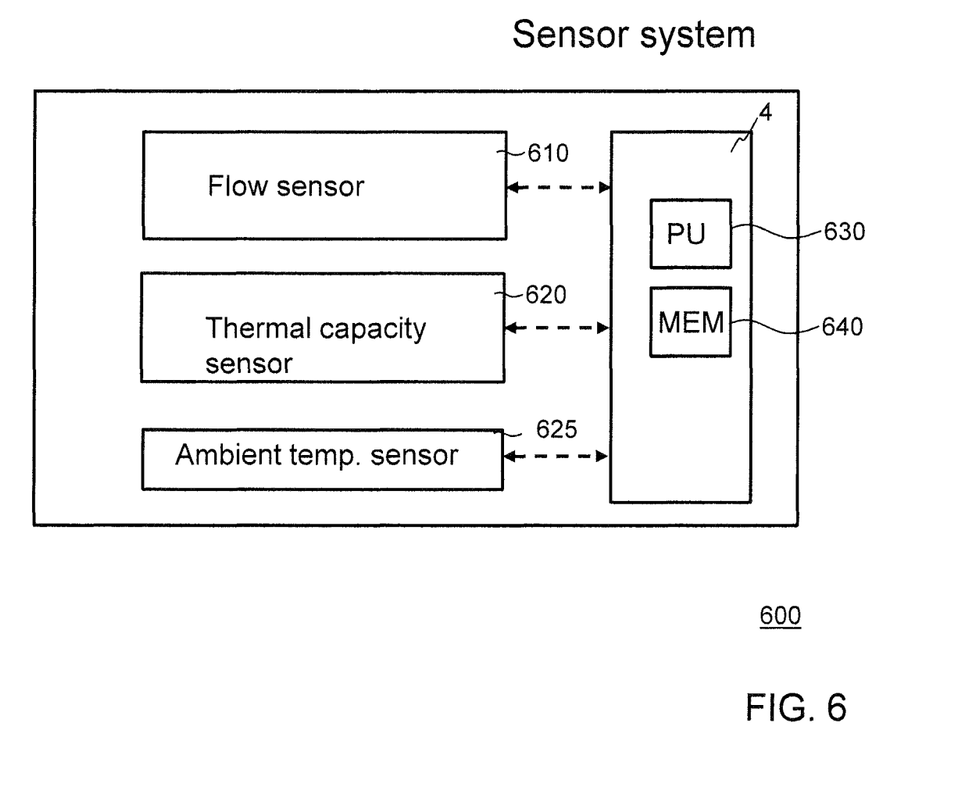
FIG. 6 shows a sensor system comprising a gas flow sensor for measuring the gas flow of a target gas and a sensor device for measuring the thermal capacity of the target gas.

FIG. 6 shows a sensor system 600 comprising a gas flow sensor 610 for measuring the gas flow of a target gas, in particular a natural gas, and a sensor device 620 for measuring the thermal capacity of the target gas. The sensor device 620 may be embodied as described above with reference to FIGS. 1 to 5. The sensor device 620 provides the determined thermal capacity of the target gas to the gas flow sensor 610. The gas flow sensor 610 may use the thermal capacity value provided by the sensor device 620 to compensate the gas dependency of the gas flow measurements, more particularly the dependence of the measured gas flow on the thermal capacity of the measured gas.

The sensor system 600 comprises a separate temperature sensor 625 which is configured to measure the ambient temperature of the natural gas. The temperature sensor 625 is arranged in particular outside the area of influence of the heating structures of the sensor device 620.

For even more accurate measurements, the temperature measured by the temperature sensor 625 can be taken into account. The measurements of the temperature sensor 625 may be used in particular to compensate for influences of the ambient temperature of the sensor system 600 on the measurement results. In other words, the thermal capacity measurements may depend on the ambient temperature of the natural gas. Hence by means of the separate temperature sensor 625 the accuracy of the thermal capacity measurements may be improved.

In this respect the sensor system 600 may perform a step 760 of the method 700 of FIG. 7. Accordingly, the sensor system 600 uses the thermal capacity that was measured/determined at the previous steps 710-750 and performs at the step 760 a compensation of the gas dependency of the gas flow sensor. This improves the measurement accuracy of the gas flow sensor.

The sensor system 600 may be in particular a system for measuring the gas flow of natural gases which may comprise a composition of a plurality of components, e.g. a hydrocarbon gas mixture comprising primarily methane, but also other components such as higher alkanes, carbon dioxide or nitrogen.

The sensor system 600 may comprise control circuity 4 for controlling the operation of the sensor device 620 and the flow sensor 610. The control circuitry 4 may encompass a processing unit (PU) 630 and a memory (MEM) 640.

As described above, the sensor device 620 determines the thermal capacity of the target gas from the temperature coefficients of the temperature dependency function of the thermal conductivity. As the thermal conductivity of gases is almost pressure independent above 500 mbar, i.e. at atmospheric conditions, the sensor device 620 provides according to embodiments of the invention the standardized volumetric heat capacity cp*$\rho_{ref}$ at standard conditions as output to the gas flow sensor 610, i.e. the volumetric heat capacity at reference temperature 0° C. and reference pressure 1013 mbar. This results finally in a measured gas flow value which is referenced to standard conditions as well.

This provides the advantage that the sensor system 600 does not need a pressure sensor to compensate for pressure dependencies of the thermal capacity of the gas. This provides advantages in terms of cost and space efficiency.

Figure 8A:
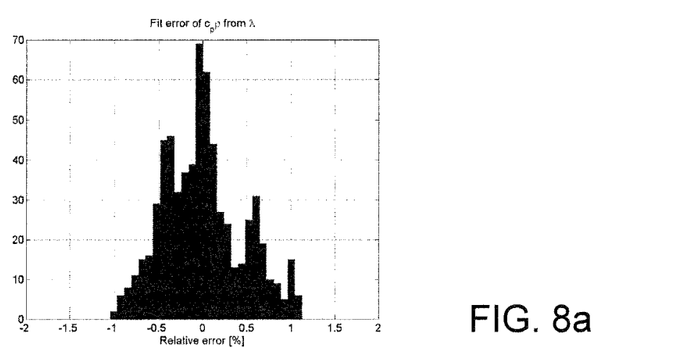
FIG. 8a shows the distribution of the relative error of the measured thermal capacity for a plurality of first sample measurements.

FIG. 8*a* shows the distribution of the relative error in % of the thermal capacity $c_p\rho$ for a plurality of first sample measurements performed for more than 500 natural gases having different compositions. The more than 500 natural gases that have been used as input for FIGS. 8*a* to 8*c* and the associated data have been collected from a plurality of databases and publications. The used data that has been taken as input for FIGS. 8*a* to 8*c* represents real data of main natural gas compositions that occur on earth.

The plurality of first sample measurements illustrated in FIG. 8*a* were performed only at a single measuring temperature for each sample gas and are hence only based on a first constant temperature coefficient. Then the thermal capacity of the target gas was determined from the first constant temperature coefficient only, based on a corresponding fitting function that is dependent only on the first constant temperature coefficient.

More particularly, the x-axis denotes the relative error in % and the y-axis the corresponding number of sample measurements that show the respective relative error.

Figure 8B:
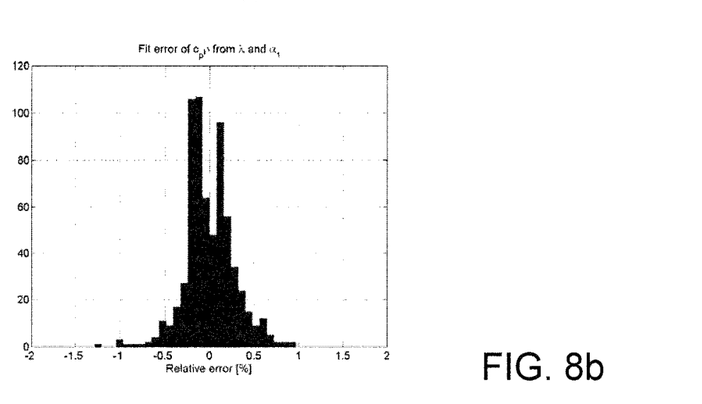
FIG. 8b shows the distribution of the relative error of the measured thermal capacity for a plurality of second sample measurements.
Figure 8C:
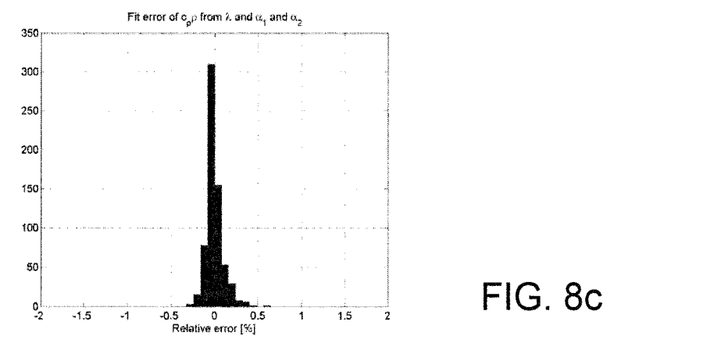
FIG. 8c shows the distribution of the relative error of the measured thermal capacity for a plurality of third sample measurements.

FIG. 8*b* shows the distribution of the relative error in % of the thermal capacity $c_p\rho$ for a plurality of second sample measurements performed for the more than 500 natural gases having different compositions as mentioned above. The plurality of second sample measurements have been performed at two different measuring temperatures for each sample gas. From these two different measurements temperatures the first constant and the second linear temperature coefficient of the temperature dependency function was determined. Then the thermal capacity of the target gas was determined from the first and the second temperature coefficient, based on a corresponding fitting function that is dependent on the first and the second temperature coefficient.

More particularly, the x-axis denotes the relative error in % and the y-axis the corresponding number of sample measurements that show the respective relative error.

FIG. 8*c* shows the distribution of the relative error in % of the thermal capacity $c_p\rho$ for a plurality of third sample measurements performed for the more than 500 natural gases having different compositions as mentioned above. The plurality of third sample measurements were performed at three different measuring temperatures for each sample. From these three different measurements temperatures the first constant, the second linear and the third quadratic temperature coefficient of the temperature dependency function was determined. Then the thermal capacity of the sample gas was determined from the first, the second and the third temperature coefficient, based on a corresponding fitting function that is dependent on the first, the second and the third temperature coefficient.

More particularly, the x-axis denotes the relative error in % and the y-axis the corresponding number of sample measurements that show the respective relative error.

As can be seen from a comparison of FIGS. 8*a* to 8*c*, taking into account the first and the second temperature coefficient significantly reduces the relative error of the thermal capacity measurement compared with measurements that only take into account the first temperature coefficient. And taking into account the first, the second and the third temperature coefficient further reduces the relative measurement errors.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The invention claimed is:

1. A sensor device for determining the thermal capacity of a natural gas, the sensor device comprising
   a substrate;
   a recess or opening arranged in the substrate;
   a first heating component and a first sensing component, the first heating component and the first sensing component extending over said recess or opening; and
   control circuitry electrically connected to the first heating component and the first sensing component and configured to control the operation of the sensor device; wherein
   the first heating component comprises a first heating structure and a temperature sensor (TS1); and
   the first sensing component comprises a temperature sensor (TS2); wherein
   the sensor device is configured to
   heat, at a first measuring step, the first heating structure to a first heating temperature;
   measure, at the first measuring step, by the temperature sensor (TS2) of the first sensing component, temperature changes at the first sensing component in dependence on the heating of the first heating structure, thereby measuring a thermal conductivity of the natural gas at a first measuring temperature;

heat, at a second measuring step, the first heating structure to a second heating temperature, the second heating temperature being different from the first heating temperature;

measure, at the second measuring step, by the temperature sensor (TS2) of the first sensing component, temperature changes at the first sensing component in dependence on the heating of the first heating structure, thereby measuring a thermal conductivity of the natural gas at a second measuring temperature;

determine a first and a second temperature coefficient of a temperature dependency function of the thermal conductivity of the natural gas at the first and the second measuring temperature; and determine the thermal capacity of the natural gas based on a fitting function, wherein the fitting function is dependent on the first and the second temperature coefficient.

2. The sensor device of claim 1, the sensor device being configured to heat, at a third measuring step, the first heating structure to a third heating temperature;

measure, at the third measuring step, by the temperature sensor (TS2) of the first sensing component, temperature changes at the first sensing component in dependence on the heating of the first heating structure, thereby measuring a thermal conductivity of the natural gas at a third measuring temperature; and determine from the first, the second and the third measuring step the first temperature coefficient, the second temperature coefficient and a third temperature coefficient of the temperature dependency function of the thermal conductivity of the natural gas at the first, the second and the third measuring temperature, wherein the fitting function is dependent on the first, the second and the third temperature coefficient.

3. The sensor device of claim 1, wherein the sensor device is further configured to compensate, by temperature measurements of the temperature sensor (TS1) of the first heating component, a drift of the first heating structure.

4. The sensor device of claim 1, wherein the sensor device comprises a housing and wherein the housing comprises a venting medium configured to allow a diffusive fluid exchange with the surrounding of the sensor device.

5. The sensor device of claim 1, wherein the first heating component is a first heating bridge being anchored in the substrate and the first sensing component is a first sensing bridge being anchored in the substrate.

6. The sensor device of claim 5, wherein the sensor device comprises a second sensing bridge comprising a temperature sensor (TS3), wherein the second sensing bridge is arranged at a different distance to the first heating bridge than the first sensing bridge.

7. The sensor device of claim 5, wherein the temperature sensors of the first sensing bridge are embodied as thermopile elements or resistive elements; and/or the temperature sensors of the first heating bridge are embodied as resistive elements or thermopile elements.

8. The sensor device of claim 5, wherein the sensor device is configured to perform a calibration procedure, the calibration procedure comprising:

adapting the fitting function to the respective temperature characteristics of the first heating bridge; and adapting the fitting function to the respective temperature characteristics of the first sensing bridge.

9. The sensor device of claim 5, wherein the sensor device comprises a second heating bridge comprising a second heating structure and a temperature sensor (TS4), wherein the first sensing bridge is arranged between the first heating bridge and the second heating bridge.

10. The sensor device of claim 9, further comprising a third heating bridge comprising a third heating structure and a temperature sensor (TS5); and a second sensing bridge comprising a temperature sensor (TS3); wherein the second sensing bridge is arranged between the second heating bridge and the third heating bridge.

11. A sensor system comprising a gas flow sensor for measuring the gas flow of a target gas and a sensor device according to claim 1, wherein the sensor device is configured to determine the thermal capacity of the target gas and to provide the determined thermal capacity of the target gas to the gas flow sensor; and the sensor system is configured to compensate a gas dependency of the gas flow sensor by means of the thermal capacity provided by the sensor device.

12. A computer program product for operating a sensor device as claimed in claim 1, the computer program product comprising a computer readable storage medium having program instructions embodied therewith, the program instructions executable by the sensor device to cause the sensor device to measure the thermal conductivity of a natural gas at the first measuring temperature;

measure the thermal conductivity of the natural gas at the second measuring temperature;

determine the first and the second temperature coefficient of the temperature dependency function of the thermal conductivity of the natural gas at the first and the second measuring temperature; and determine the thermal capacity of the natural gas based on the fitting function, wherein the fitting function is dependent on the first and the second temperature coefficient.

13. A sensor device for determining the thermal capacity of a natural gas, the sensor device comprising a substrate;

a recess or opening arranged in the substrate;

a first heating bridge being anchored in the substrate and a first sensing bridge being anchored in the substrate, the first heating bridge and the first sensing bridge extending over said recess or opening, the first heating bridge comprising a first heating structure and a temperature sensor (TS1) and the first sensing bridge comprising a temperature sensor (TS2);

a second heating bridge comprising a second heating structure and a temperature sensor (TS4), wherein the first sensing bridge is arranged between the first heating bridge and the second heating bridge;

a third heating bridge comprising a third heating structure and a temperature sensor (TS5);

a second sensing bridge comprising a temperature sensor (TS3); wherein the second sensing bridge is arranged between the second heating bridge and the third heating bridge; and control circuitry electrically connected to the first heating bridge, the second heating bridge, the third heating bridge, the first sensing bridge and the second sensing bridge, the control circuitry being configured to control the operation of the sensor device;

wherein the sensor device is configured to heat, at a first measuring step, the first, the second and the third heating structure to a first heating temperature;

measure, at the first measuring step, by the temperature sensors of the first and the second sensing bridge, temperature changes at the first sensing bridge and the second sensing bridge in dependence on the heating of the first, the second and the third heating structure;

heat, at a second measuring step, the first and/or the second heating structure to a second heating temperature, the second heating temperature being different from the first heating temperature;

measure, at the second measuring step, by the temperature sensors of the first and the second sensing bridge, a differential temperature signal of the temperature difference between the first and the second sensing bridge;

determine from the first and the second measuring step a first temperature coefficient and a second temperature coefficient of a temperature dependency function of a thermal conductivity of the natural gas; and determine the thermal capacity of the natural gas based on a fitting function, wherein the fitting function is dependent on the first and the second temperature coefficient.

14. The sensor device of claim 13, wherein the sensor device is configured to heat, at a third measuring step, the first and/or the second heating structure to a third heating temperature, the third heating temperature being different from the first and the second heating temperature;

measure, at the third measuring step, by the temperature sensors of the first and the second sensing bridge, a differential temperature signal of the temperature difference between the first and the second sensing bridge; and determine from the first, the second and the third measuring step the first, the second and a third temperature coefficient of the temperature dependency function.

15. The sensor device of claim 13, wherein the sensor device is configured to repeat the first and the second measuring step with different heating temperatures.

16. A method for determining the thermal capacity of a natural gas, the method comprising measuring a thermal conductivity of the natural gas at a first temperature;

measuring a thermal conductivity of the natural gas at a second temperature;

determining a first and a second temperature coefficient of a temperature dependency function of the thermal conductivity of the natural gas at the first and the second temperature; and determining the thermal capacity of the natural gas based on a fitting function, wherein the fitting function is dependent on the first and the second temperature coefficient.

* * * * *